United States Patent [19]

Glanz et al.

[11] 4,335,316
[45] Jun. 15, 1982

[54] WEB BREAK DETECTOR WITH ADJUSTABLE SCANNING HEAD

[75] Inventors: Richard Glanz, Crystal Lake; Sun C. Chang, Naperville, both of Ill.

[73] Assignee: Baldwin-Korthe Web Controls, Inc., Addison, Ill.

[21] Appl. No.: 138,499

[22] Filed: Apr. 9, 1980

[51] Int. Cl.³ ............................................. G01N 21/88
[52] U.S. Cl. ..................................... 250/572; 250/221
[58] Field of Search ............... 250/221, 562, 563, 572, 250/214 AL

[56] References Cited

U.S. PATENT DOCUMENTS 4,207,466 6/1980 Drage et al. .................... 250/221 X
4,282,430 8/1981 Hatten et al. ........................ 250/221

Primary Examiner—David C. Nelms
Assistant Examiner—Darwin R. Hostetter
Attorney, Agent, or Firm—Neuman, Williams, Anderson & Olson

[57] ABSTRACT

A system for detecting breaks in a web moving through a predetermined area including a scanner head assembly having an infrared emitter, optical filtering and an adjustable receiver for detecting the presence or absence of reflecting infrared radiation from an object within the scanner path. The scanner control system provides a power source for the emitter which pulsates at a predetermined frequency and low duty cycle, a receiver circuit incorporating selective filtering, and a phase-locked detector loop tuned to the emitter frequency for optimum selectivity and performance in the face of varying ambient light conditions. A scanner head having a linearly adjustable operating range is employed for tailoring the system to a wide range of web locations and conditions.

17 Claims, 5 Drawing Figures

WEB BREAK DETECTOR WITH ADJUSTABLE SCANNING HEAD

BACKGROUND OF THE INVENTION

This invention relates to web break detector systems in general and more specifically to web break detection systems utilizing photoelectric principles.

Optical scanning systems have for many years been used to monitor the condition of moving webs of paper, cloth and the like in processing mills and printing presses. The object of such devices is to rapidly detect tears and other discontinuities in the web, and in particular along the edges of the web. Such devices then shut down or otherwise disable the equipment before the break can increase in size and accumulate the running material in or around the many rollers and other operating mechanisms of the press. In view of the extremely high speed at which many webs travel, a minor tear can cause a major equipment breakdown when all or a portion of the web begins to accumulate within the system. Typically, therefore, web break detectors are used not only to shut down systems but to energize automatic web cutting blades to immediately stop the flow of the web through the equipment.

In optical web guide detectors, light sources have been used that emit in the infrared region. Filtered detectors have been employed to detect the infrared emission while being generally nonresponsive to the light environment outside of the infrared spectrum. A system of this type incorporating a synchronized and pulsating type infrared detection system is shown in U.S. Pat. No. 3,906,232 of Meihofer. As noted therein, early photoelectric web break systems positioned the receiver on the opposite side of the web from the emitter. However, due to the desirability of detecting a slackening of the web as well as web breaks, the receiver and detector have in recent history been positioned on the same side of the web so that the system scans for continuous reflection of the emitted light from the web surface. Properly adjusted, systems of this type can be responsive to both breaks and slackenings of the web which cause the web to move outside of a predetermined zone defined by the scan head optics.

Systems of the foregoing type have had several limitations, however. Since they are dependent upon the reflection of light from the web, they are sensitive to variations in the web position which alter the angle of light reflection between the transmitter and receiver. Since this angle has been fixed in previous systems, there is only one optimum position for the web to be traveling in. The range of permissible variation from that position is quite small. Second, prior reflection-type scan systems have been extremely sensitive to variations in the web color and texture, since both of these factors affect the reflectivity of the surface being monitored. Of course, a dark colored web obviously absorbs more light and reflects less. Hence, its detectability is more limited than is the detectability of a lighter colored shiny web. However, if the system optics and sensitivity of the prior systems are adjusted to accommodate the dark, coarse web, problems may arise in the presence of a white shiny web in that so much light is reflected at so many angles that the optics and electronics of the receiver are essentially saturated and insensitive to the minor light variations that occur when the web begins to separate or tear.

Some prior art systems have attempted to solve the foregoing problems by electrical adjustments of the gain and sensitivity in the receiver circuitry. However, such adjustments are difficult to implement due to the inherent nonlinearities between system response to various colors and web locations. While the system may be capable of detecting both white and black webs at one web location, its ability to handle both color variations will be nonexistent at other web locations due to the angular differences of light reflection.

SUMMARY OF THE INVENTION

The present invention overcomes the aforesaid limitations of the prior art systems through the provision of a variable range scanning head which is adjustable in a substantially linear fashion to accommodate various web colors, textures and distances from the scanning head. More specifically, it is an object of the present invention to provide a break detection system and scanning head which can operate over a broad range of web locations while maintaining maximum immunity to ambient light conditions. This system has the further advantage of enjoying the economy of operation inherently available from pulsed infrared detection systems.

These and other objects and advantages are accomplished through the provision of an optical receiver which responds to the frequency of the emitted infrared radiation in a highly selective manner without the necessity for synchronization of the transmission and reception pulses. Selectivity in the receiver is accomplished through the provision of an optical infrared filter, a high-pass electrical filter, and a phaselocked loop frequency detector having sharp cutoff characteristics. Detector range control is provided by a linearly variable scanning head designed for optimum selectivity and immunity to ambient light conditions.

As such, the present system eliminates the need for synchronization between the emitter and detector and the corresponding need for accurate control of the delays in the emitter and receiver channels. The system further eliminates the need for electrical control of sensitivity and system gain as well as the need for accurate establishment of threshold levels for proper discrimination. In short, it is essentially a frequency mode detection system rather than one relying solely on amplitude and phase.

Other objects and advantages of the invention will become apparent upon reading the following detailed description and the appended claims and upon reference to the accompanying drawings.

BRIEF DESCRIPTION OF THE DRAWINGS

In the drawings:

FIG. 3 is a side elevational view of the optical assembly for each of the two scanners shown in FIG. 1 with a diagrammatic illustration of the operating characteristics of the scanner head.

FIG. 4 is a graph illustrating the approximate relationship between manual adjustment of the scanner head and the scanner sensitivity.

FIG. 5 is a side elevational view of an alternative embodiment of the scanner head optical assembly which may be utilized with the present invention.

While the invention will be described in connection with certain preferred embodiments, it will be understood that we do not intend to limit the invention to those embodiments. On the contrary, we intend to cover all alternatives, modifications and equivalents as may be included within the spirit and scope of the invention as defined by the appended claims.

DESCRIPTION OF THE PREFERRED EMBODIMENTS

Figure 1:
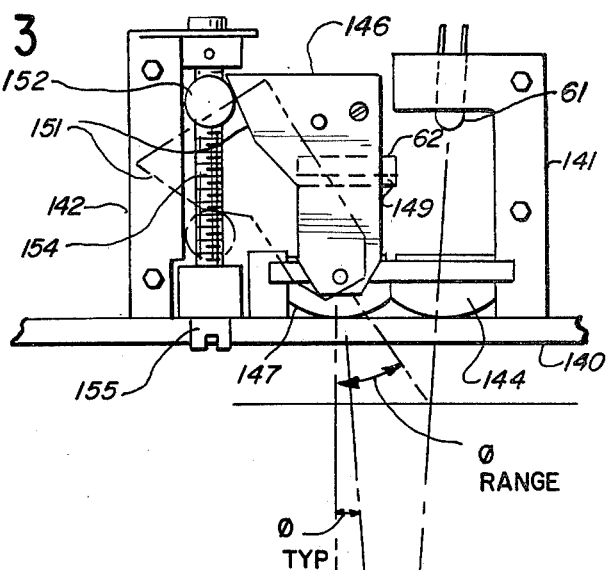
FIG. 1 is a simplified illustration of the web break detection system of the present invention in a press control environment.

Turning now to the drawings, FIG. 1 depicts a scanner bar assembly 10 having a pair of optical scan heads 12 and 14 spaced apart to scan the opposite edges of a moving web 16. As depicted, the web is moving between a pair of rollers 18, 20 which may be located at any of a plurality of locations along the moving web. While two scan heads 12, 14 are shown in the embodiment of FIG. 1, it will be apparent that additional scan heads could be provided to monitor the center or any other position across the web path. Similarly, a single scan head could provide the monitoring function in certain applications. Scanning along the edge of the web is preferred in view of the fact that most tears or breaks in the web being along the edges. Each of the scan heads 12, 14 has an output line 22, 24 respectively, for signaling the various controls and interlocks that stop the press in the instance of a web break. The press stop controls are depicted generally at 26. While it is contemplated that the control circuits and the optical transceiver will all be integral with the scanner head within the scanner bar 10, it will be appreciated that the optical and electrical portions could be separate and apart from each other without departing from the spirit and scope of the invention.

Figure 2:
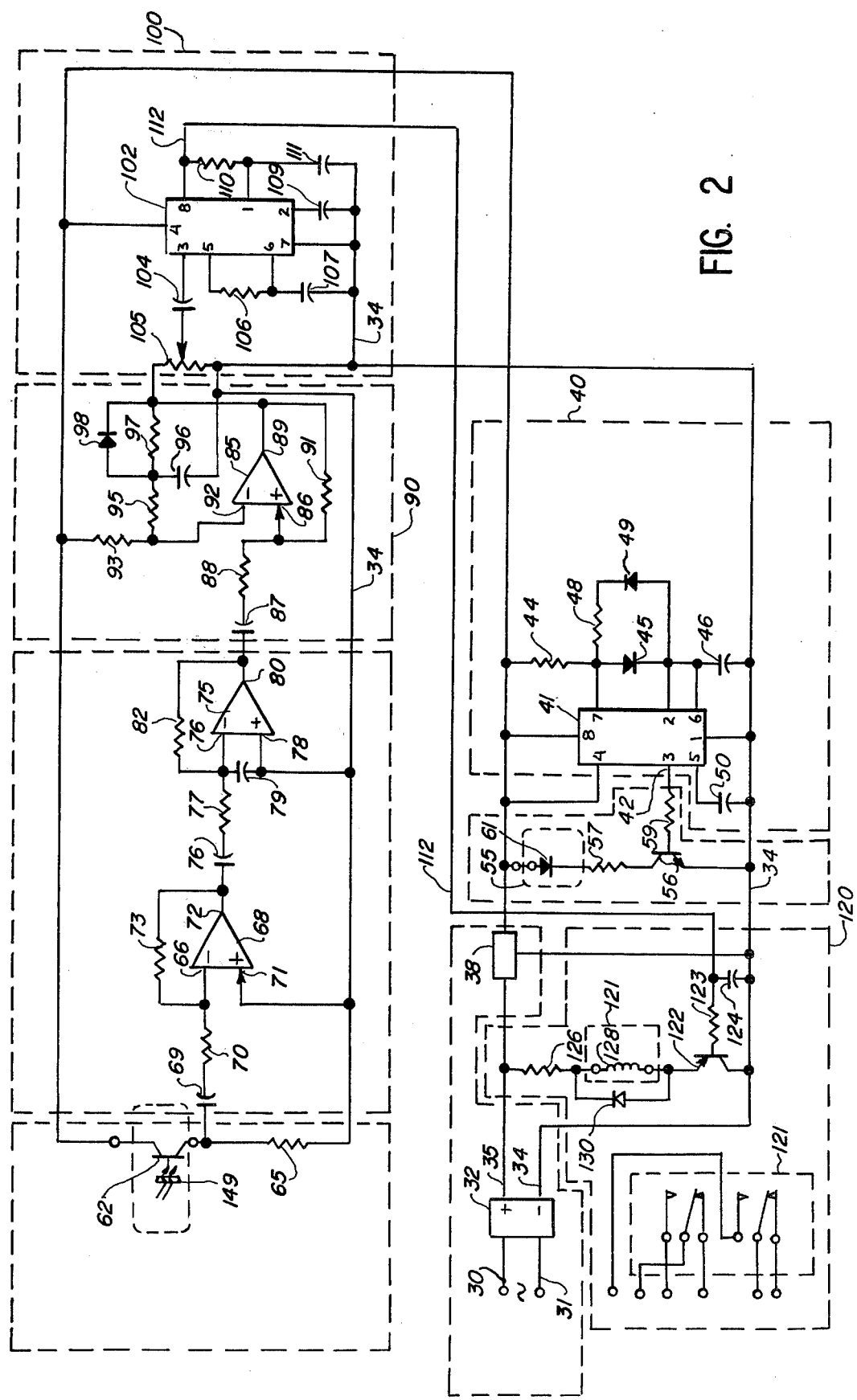
FIG. 2 is a schematic diagram of the transmission and detector circuit incorporated in each of the scanners shown in FIG. 1.

FIG. 2 depicts the control circuits used with the present invention. The AC input at lines 30, 31 is converted to a DC supply voltage by a power supply circuit 32 which may be any of a plurality of conventional types. The output voltage from the supply circuit appears across a ground or common line 34 and a positive supply line 35. While the full supply voltage, typically 20 volts, is used for the relay driver and output circuit to be described below, a lower voltage, typically 5 volts DC, is provided for the transmitter and receiver circuitry through the incorporation of a voltage regulator 38 coupled to the positive supply line 35 and referenced to the ground line 34.

For the purpose of generating a pulsating current for the infrared emitting diode, there is provided a free-running astable multivibrator depicted generally at 40. While this circuit may be any of a variety of different circuits producing a constant frequency output signal of short duration, the circuit shown incorporates a type 555 Timer chip manufactured by Signetics, Inc. The timer circuit is connected between the regulated supply voltage and ground and is appropriately biased as shown to provide an output signal on line 42 having a short duty cycle, typically 3%, and a frequency of 1100 Hz. While the timer circuit 41 may have any of a variety of different configurations depending upon the manufacturer, the biasing network in the present instance includes a resistor 44, a diode 45 and capacitor 46 connected in a series circuit between the positive regulated supply and ground. In parallel with the diode 45 is a series circuit which includes a resistor 48 and diode 49 which is poled opposite to the diode 45. Pins 4 and 8 of the timer device are connected to the regulated positive supply while pins 1 and 5 of the device are coupled to ground, the latter being coupled through a capacitor 50. Pins 2 and 6 are connected to the junction between the capacitor 46 and 45, while pin 7 is connected to the junction between resistors 44 and 48 and diode 45. The multivibrator circuit 40 provides a highly stable output frequency at pin 3 thereof while consuming very little power due to the short duty cycle of its output pulses on the line 42.

A radiation source depicted generally at 55 is driven from the output line 42 of the timer circuit 41 through a drive transistor 56 of the NPN variety. The emitter of the transistor 56 is coupled to ground while the collector is in series with the radiation source 55 and a resistor 57. The base of the transistor 56 is driven by the output line 42 through a series resistor 59. While the radiation source 55 may be any of a variety of different devices, it is here depicted as including the infrared-emitting diode 61 which is typically part of a matched optical pair with an infrared sensitive transistor 62 located in the receiver assembly to be described below.

As shown in FIG. 3 and described more fully below, the infrared-emitting diode 61 is positioned on an angle with respect to the desired web path and focused through optical devices to be reflected back to the photosensitive transistor 62 mounted in an adjustable receiver assembly.

Returning to the control circuit of FIG. 2 and in particular to the receiver section shown in the upper portion of the figure, the phototransistor 62 controls the current between its emitter and collector and thus varies the voltage developed across a resistor 65 connected in series with the transistor 62 between the regulated positive supply and ground. The signal across the resistor 65 is coupled to the inverting input 66 of an operational amplifier 68 through an RC series circuit including a capacitor 69 and resistor 70. The noninverting input terminal 71 of the amplifier 68 is referenced to ground, while the output terminal 72 has its signal fed back to the inverting input 66 through a feedback resistor 73. As thus connected, the amplifier 68 provides current amplification and a high-pass filtering stage for the signal received by the phototransistor 62. A second stage of amplification and high-pass filtering is provided by an operational amplifier 75, the inverting input terminal 76 of which is connected to receive the output of the amplifier 68 through an A-C coupling capacitor 76 and resistor 77. The noninverting input 78 of the amplifier is referenced to ground and coupled to the inverting input 76 through a capacitor 79, while the output terminal 80 is connected back to the input terminal 76 through a feedback resistor 82. Of course, each of the operational amplifiers described herein additionally has ground and DC supply potentials connected thereto, but these are not shown in the drawings. As thus far described, the amplifiers 68 and 75 provide amplification and high-pass filtering for the signal taken from the phototransistor 62 in the receiver side of the scanning head. As such they render the receiver circuitry substantially immune to ambient light conditions of a steady state or slowly varying nature.

For the purpose of shaping and conditioning the output signal from the amplifier 75, there is provided a one-shot circuit 90 which receives the amplifier output signal, generally in the shape of a train of irregularly shaped spikes, and converts them into a square wave having a constant amplitude and approximately a 50% duty cycle. While any of a variety of one-shot circuits may be employed for this purpose, there is shown an operational amplifier 85 having a noninverting input 86 for receiving the output of the amplifier 75 through a series capacitor 87 and a resistor 88. An output terminal 89 from the amplifier 85 provides feedback to the noninverting input terminal 86 through a resistor 91. The amplifier 85 also has an inverting input terminal 92 referenced to the positive supply line through a series resistor 93. Control of the pulse width of the output signal from the amplifier 85 is provided by an RC timing network consisting of a resistor 95 and capacitor 96 coupled between the inverting input terminal 92 and ground. The junction between the capacitor 96 and resistor 95 is also coupled to the output of the amplifier 85 through a resistor 97 which is in parallel with a diode 98. In operation, a positive-going signal from the output of the amplifier 75 at the input of the one-shot circuit 90 is applied to the noninverting input terminal 86 of the amplifier 85 and causes the output terminal 89 of the amplifier 85 to immediately go from ground potential toward the positive supply voltage. The rise time of the output pulse will be determined by the ratio of the feedback resistance 91 to the input resistance 88, which is typically very high. As the output voltage at terminal 89 goes positive, the capacitor 96 begins to charge, raising the potential at the inverting input terminal 92 of the amplifier 85 in a gradual fashion until it exceeds the potential at the noninverting terminal 86. At this point the output voltage from the terminal 89 falls rapidly to ground potential and remains there until another input pulse is received from the amplifier 75. By controlling the value of the resistor 95 and capacitor 96 to provide a 0.4 millisecond pulse width at the output terminal 89, the one-shot circuit 90 serves to optimize the duty cycle for the signal sought to be detected by the circuit, namely the 1100 Hz pulsating infrared signal generated by the emitter circuitry.

The pulse train output from the one-shot circuit 90 is, in turn, coupled to a phase-locked loop circuit 100 which operates as a narrow band detector sensitive to the 1100 Hz emission frequency within a tracking range varying ±7%. While a variety of different commercial devices may be used for this application, the phase-locked loop circuit 100 is depicted as employing a model 567 Tone Decoder manufactured by Signetics, Inc. While the manufacturer's specifications for this device and for the timer circuit 41 of the emission circuitry are incorporated herein by reference, it is noted that the input at terminal 3 of the tone decoder circuit 102 is received through a coupling capacitor 104 from the wiper of a variable potentiometer 105 coupled between ground and the output of the oneshot circuit 90. The bandwidth for the tone detector is adjusted by appropriate selection of a value for a capacitor 109 connected between terminal 2 of the tone decoder 102 and ground. A resistor 106 in series with a capacitor 107 connects terminal 5 to ground, while terminal 6 is connected to the junction between the aforesaid resistor 106 and capacitor 107. The output is available on terminal number 8 and is referenced to ground through a series resistor 110 and capacitor 111, the junction between the resistor 110 and capacitor 111 being coupled to terminal number 1 of the decoder 102. Terminal 7 is grounded and terminal 4 is connected to the positive supply. The output at terminal 8 is provided on a line 112.

In operation, the phase-locked loop generates an output whenever the 1100 Hz component of the input signal from the phototransistor 62 exceeds a predetermined level established by the variable resistor 105 acting as a sensitivity control. So long as the web continues to reflect radiation onto the phototransistor 62, the output on line 112 remains at a low potential. A high voltage level on line 112 signal a break in the web or sufficient slack in the web to cause the web to deviate from its desired path, signalling a dangerous condition.

For the purpose of responding to the detection of the 1100 Hz signal in the phase-locked loop 100 there is provided a relay driver/output circuit 120 which includes a plurality of switches 121 adapted to deactivate the press and/or energize the severing device to break the web. The circuit 120 includes a PNP-type transistor 122 operating in a grounded collector configuration and having its base electrode driven from the output line 112 of the phase-locked loop through a series resistor 123 with a shunt capacitor 124 connected to ground. The emitter of the transistor 122 controls current flows through a series path consisting of a resistor 126 and the solenoid 128 of the relay 121. For protection there is provided a diode 130 in parallel with the relay solenoid 128. As thus connected, the relay 121 is deactivated so long as the signal on the output line 112 from the phase-locked loop 100 remains high. Upon occurrence of a break in the web or slackening as aforesaid, the potential on the line 112 goes high, deactivating the transistor 122 and de-energizing the relay 121. The contacts of the relay 121 may be incorporated in appropriate press controls that may include additional contacts as needed.

In accordance with another aspect of the present invention, there is provided an optical scanning head shown in FIG. 3 which is particularly well adapted for web monitoring of this type in that it is linearly adjustable to provide optimum response to both light and dark web portions at a variety of nominal web positions. More specifically, the optical scanner includes a frame structure including a horizontal member 140 and a pair of integral support members 141 and 142 for supporting respectively the emitter diode 61 and the receiver control mechanism to be described. The entire optical scanner assembly shown in FIG. 3 is adapted to fit into various locations along the scanner bar 10 shown in FIG. 1 in a modular configuration that includes the electronics as well. To this end fasteners (not shown) normally attach the horizontal member 140 to the scanner bar 10.

The emitter assembly further includes a lens 144 for optically focusing the infrared transmission. A flat glass (not shown) protects the scanner from the outside environment. Radiation emitted by the diode 61 passes through the lens 144 and through an aperture provided in the frame member 140 onto the passing web. For receiving the reflected radiation, the scanner head includes a receiver assembly, including the radiation responsive transistor element 62 which is fixedly mounted on a pivotable carriage 146. As with the optical channel for the emitter, the optical channel for the receiver includes a lens 147 which is affixed to the frame and convex in form to allow reception of the radiation from the web over a variety of angles. The pivotable carriage 146 also has an optical filter 149 of the infrared type located immediately below the radiation responsive transistor 62.

For the purpose of providing a linear adjustment of the receiver assembly, the pivotable member 146 has a cam surface 151 thereon which is biased toward a cam actuator 152 by spring means (not shown). The cam actuator 152 is cylindrical in nature and has a hole therethrough for accepting a threaded shaft 154 which is rotatable from its lower end by a screw driver receptacle 155. The irregular shape of the cam follower surface 151 of the pivotable member 146 serves to linearize the relationship between the setting of the screw adjustment 155 and the optimum detection distances between the scanner head assembly and the web. This relationship is shown in the graph of FIG. 4 wherein the revolutions of the adjusting screw 155 is plotted against the maximum distance for web detection. While the curves of the graph of FIG. 4 are only approximate, it is noted that the relationship of optics adjustment to the maximum distance between the web and the scanner head is nonlinear when the angle of the pivotable carriage 146 varies directly with the turns of the adjusting screw 155 (see Curve A). With the cam follower surface 151, however, the maximum permissible range varies substantially linearly with the turns of the adjusting screw 155 (Curve B).

The significance of linearizing the manual adjustment is shown in FIG. 3 wherein various horizontal lines are provided to show the maximum and minimum ranges for detection of both black and white surfaces for a typical angle $\phi_{TYP}$. It will be noted that the range over which a course black web can be detected is substantially narrower than that over which a white shiny web can be detected. Therefore, as the web moves farther away from the scanner head from the optimum web position shown, it may first reach a region in which black portions can not be distinguished from breaks. This system will thereafter be sensitive only to breaks in a white web. As the web is moved still further from the optimum web position for the receiver angle $\phi_{TYP}$ it will reach an area in which breaks can not be detected regardless of the color and texture of the web. Through the adjustable mechanism described above, the angle $\phi$ can be varied over a range of approximately 30° from the vertical so that the point of optimum reflection from the emitter to the receiver off the web can be adjusted accordingly. With the optic system as shown in FIG. 3 it has been found that web locations can be varied from ½ inch to 12 inches for black webs and from ½ inch to approximately 20 inches for white webs and still remain within the detectable region of the scanner head by proper adjustment of the screw control 155.

While the scanner head assembly of FIG. 3 is suitable for most detection purposes and provides a wide operating range, for certain applications it may be desirable to have the emitter angle vary in a manner similar to that of the receiver angle. A system designed to operate in this manner is shown in FIG. 5, which differs from FIG. 3 only in that the emitter diode 61 is mounted on a second pivotable member 170. Affixed to the pivotable members 146 and 170 are a pair of toothed gear segments 173 and 174 respectively which intermesh to allow the focus beams for the emitter and receiver optics to converge and diverge equally under the control of the screw adjustment 155. In this manner, greater directivity and sensitivity can be obtained because the optical axis of the transmitter and receiver portions of the scanner head will be always aligned with the optimum receiver angle. Hence greater immunity to responsiveness to ambient light conditions can be obtained.

It will be apparent from the foregoing that while the embodiment described operates with the optical receiver and emitter on the same side of the web path, the system of frequency modulation and detection of the present invention is also applicable where the receiver and radiation source are on opposite sides of the web. In the latter case the relay drivers and output circuit 120 is modified to disable the press and/or activate the web severing blades whenever the radiation from the source passes to the receiver without obstruction by the moving web. In such a direct optical system, the emitter and receiver can be somewhat simplified and need not be variable, but the advantages of infrared modulation and frequency selective reception are retained.

From the foregoing, it should be apparent that there has been brought to the art a web break detector system which is highly immune to ambient light conditions and which provides an operating range which is vastly improved over systems heretofore known in the art. At the same time, the system is economical to construct and uses very little energy during operation due to the pulsating nature of the optical system.

We claim as out invention:

1. A system for signalling the occurrence of discontinuities in a moving web in a printing press or the like wherein the web position perpendicular to its direction of travel varies within a predetermined range, comprising:

a radiation source positioned and aimed so that its beam intersects the web path;

means for activating said radiation source at a predetermined pulse frequency such that its beam intersects said web path in a pulsating manner;

optical receiver means positioned to receive at least a portion of the beam reflected from said radiation source so long as the web is within said predetermined lateral range and adapted to produce an electrical output signal which varies in accordance with the received radiation;

frequency detector means coupled to said receiver means for producing an output signal indicative of the presence of said predetermined frequency in the frequency spectrum of said receiver output signal; and, means responsive to said detector output for instantaneously manifesting the occurrence of a web break whenever said predetermined frequency is not present in the spectrum of said receiver output signal.

2. A web break detection system according to claim 1 wherein said radiation source produces an output in the infrared region and wherein said system further includes an optical filter associated with said optical receiver means for blocking from said receiver means all radiation outside of the infrared spectrum.

3. A web break detection system according to claim 1 wherein said detector means includes a phaselocked loop adjusted to produce an output signal only in response to said predetermined frequency.

4. A web break detection system according to claim 1 wherein said radiation source is substantially directional and focused along a fixed predetermined axis which intersects the web path and wherein said optical receiver means is manually adjustable so that its focus axis may be varied linearly with respect to the axis of said radiation source so as to provide control over the sensitivity of said receiver means.

5. A web break detection system according to claim 4 wherein said receiver means is mounted on a common frame with said light source and wherein said system further includes a manual control and means for providing a substantially linear relationship between the position of said manual control and the distance between said common frame and the intersection of the focus axes of said radiation source and receiver means.

6. A web break detection system according to claim 5 wherein said means for providing a linear relationship includes a non-linear cam affixed to said optical receiver means, a support bracket pivotally coupled to said cam and said optical receiver means, and a moveable cam follower whose position is manually adjustable relative to said cam so as to pivot the optical receiver.

7. A system for detecting discontinuities in a moving web positioned within a predetermined range lateral to the path of web travel comprising in combination:
a radiation source positioned and aimed so that its beam intersects the web path;
means for activating said radiation source at a predetermined frequency such that its beam radiates upon said web path in a pulsating manner;
optical receiver means positioned with respect to said radiation source and said web path so that its reception of radiation from said source is a function of the continuity of the web surface, so long as the web surface remains within said predetermined lateral range, said receiver means being operative to produce an electrical output signal which varies in accordance with the received radiation;
frequency detector means coupled to said receiver means for producing an output signal indicating the presence of said predetermined frequency in said receiver output signal; and
means coupled to said frequency detector for instantaneously stopping movement of said web upon the occurrence of a discontinuity in said frequency detector output signal.

8. A system according to claim 7 for detecting discontinuities in a moving web wherein said optical receiver means is positioned on the same side of the web path as said radiation source and armed at the web such that its reception of radiation from said source depends on reflection from said web of said radiation beam.

9. A system according to claim 7 for detecting discontinuities in a moving web wherein said optical receiver means is positioned on the opposite side of the web path from said radiation source such that its reception of said radiation beam occurs whenever a discontinuity of said web allows said radiation beam to pass from said radiation source to said receiver.

10. A system for detecting discontinuities in a moving web in a printing press, said web being moveable within a predetermined range lateral to its path of movement, comprising in combination:
a radiation source positioned and aimed so that its beam intersects the web path;
means for activating said radiation source at a predetermined frequency such that its beam intersects said web path in a pulsating manner;
optical receiver means positioned with respect to said radiation source and said web path so that its reception of radiation from said source is a function of the continuity of the web surface so long as the web is within said predetermined lateral range, said receiver means being operative to produce an electrical output signal which varies in accordance with the received radiation;
a signal conditioning circuit responsive to said receiver output signal and adapted to produce a pulse in response to each variation in the amplitude of said receiver output signal, each of which pulses has a width corresponding to that of a square wave occurring at said predetermined frequency;
frequency detector means for receiving said train of pulses and producing an output signal which varies with the detection of said predetermined frequency in said output signal and
means for disabling said press instantaneously upon an interruption of said output signal due to a discontinuity in the signal being detected.

11. A system according to claim 10 for detecting discontinuities in a moving web further including a high-pass filter circuit coupled between said receiver means and said signal conditioning circuit for inhibiting variation in said receiver output signal resulting from ambient light conditions.

12. A system for detecting discontinuities in a web positioned within a predetermined range lateral to the direction of web travel, said system comprising:
a radiation source positioned adjacent the web path whose radiation spectrum is substantially limited to the infrared region;
means for pulsating said radiation source at a predetermined frequency;
optical receiver means positioned with respect to said radiation source for receiving said infrared radiation whenever it is reflected off a web moving within said web path within said lateral range, said optical receiver means including a radiation transducer for producing an output signal that varies with the received radiation level and an optical filter between said web and said transducer that is adapted to inhibit the passage of radiation outside the infrared region;
a high-pass filter for receiving said receiver output signal and removing therefrom low frequency variations resulting from ambient light conditions;
a frequency detector for producing an output signal responsive substantially exclusively to the occurrence of said predetermined frequency in the spectrum of said receiver output signal, and
means coupled to said frequency detector for instantaneously signalling the interruption of said detector output signal.

13. A system according to claim 12 wherein said means for pulsating said radiation source operates with a very low duty cycle and wherein said system further includes a signal conditioning circuit between said optical receiver means and said frequency detector for restoring said receiver output signal to approximately a fifty percent duty cycle to facilitate detection of said predetermined frequency by said frequency detector.

14. A photoelectric scanning head for detecting a web within a selected spacial region comprising:
a frame member positioned adjacent said spacial region;
a radiation source affixed to said frame and adapted to radiate across said spacial region substantially along a fixed transmission axis;
a photoresponsive receiver moveably coupled to said frame and focused to receive radiation reflected from said web substantially along a predetermined reception axis; and,
means for varying the angle of said reception axis with respect to said transmission axis including a manual control and a non-linear cam surface responsive to said manual control for adjusting the point of intersection of said transmission and reception axis in a substantially linear manner with respect to movement of said manual control.

15. A method for detecting the presence of irregularities in a web moving along a predetermined path in a printing press or the like comprising:

generating a beam of radiation across said predetermined path;

modulating said radiation beam at a selected frequency;

monitoring the reflection of said radiation beam from said web that occurs whenever the web is continuous within said path and producing an electrical signal that varies with the intensity of said reflected radiation; and, detecting said selected frequency in said electrical signal as an indication of continuity of the web within said predetermined path, and instantaneously disabling the press upon the occurrence of an interruption in the continuity of the detection of said selected frequency.

16. The method of claim 15 for detecting the presence of irregularities in a web moving along a predetermined path further comprising the step of filtering the electrical signal to remove low frequency variations resulting from ambient light conditions.

17. A method of claim 15 for detecting the presence of irregularities in a web moving along a predetermined path wherein said generated beam of radiation occurs substantially in the infrared region and wherein said method further includes the step of optically filtering the radiation reflected from said web for substantially inhibiting the monitoring of radiation outside said infrared spectrum.

* * * * *